US00PP22920P2

(12) United States Plant Patent
Kordes

(10) Patent No.: US PP22,920 P2
(45) Date of Patent: Aug. 7, 2012

(54) HYBRID TEA ROSE PLANT NAMED 'KORARTISCH'

(50) Latin Name: *Rosa hybrida*
Varietal Denomination: KORartisch

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,244

(22) Filed: Oct. 14, 2010

(51) Int. Cl.
*A01H 5/00* (2006.01)

(52) U.S. Cl. ..... Plt./137

(58) Field of Classification Search ..... Plt./137, Plt./138, 148, 149
See application file for complete search history.

*Primary Examiner* — June Hwu

(57) ABSTRACT

A new and distinct variety of rose with long lasting, novel pink flowers, and attractive foliage with good disease resistance. It exhibits upright growth with abundant flowers. The new variety propagates well by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORartisch'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2000. The crossing was between an unnamed seedling and another unnamed seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORartisch'.

SUMMARY OF THE INVENTION

The new rose plant may be distinguished from its seed parent, an unnamed seedling, by the following combination of characteristics:

1. Flowers are borne singly on the stems of 'KORartisch'. Flowers are borne in clusters on the stems of the seed parent.
2. The petal count of 'KORartisch' is very double. The petal count of the seed parent is semi-double.

The new rose plant may be distinguished from its pollen parent, an unnamed seedling, by the following combination of characteristics:

1. 'KORartisch' grows with an upright habit. The pollen parent grows with an arching habit.
2. General tonality of the open flower of 'KORartisch' is Red-Purple Group 58C. General tonality of the open flower of the pollen parent is Red-Purple Group 67B.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORartisch' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORartisch' was selected in May, 2001 from the seedling beds to be asexually propagated for further evaluation. The first asexual propagation of 'KORartisch' was done by budding to seedling understocks in July, 2001 at the inventor's nursery in Offenseth-Sparrieshoop, Germany.

This initial and other subsequent propagations conducted in controlled environments demonstrate that 'KORartisch' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORartisch'.

DETAILED BOTANICAL DESCRIPTION

The following is a description of 'KORartisch', as observed growing in October, 2010 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORjuknei', a rose variety from the same inventor described and illustrated in U.S. Plant Pat. No. 22,499.

CHART 1

| Characteristic | 'KORartisch' | 'KORjuknei' |
|---|---|---|
| Petal count | 150 | 100-120 |
| Bud form | Globular | Short, pointed ovoid |
| Pistils | 50 | 30 |

Parents:

*Seed parent*.—An unnamed seedling.

*Pollen parent*.—An unnamed seedling.

Classification:

*Botanical classification*.—*Rosa hybrida*, 'KORartisch'.

*Commercial classification*.—Hybrid Tea rose.

FLOWER AND FLOWER BUD

Blooming habit: Recurrent.

Flower bud:

*Size*.—Upon opening, 30 mm in length from base of receptacle to end of bud and 35 mm diameter at its widest point.

*Bud form*.—Short. Globular.

*Bud color*.—As sepals first unfold, bud color is Red Group 53C. When ¼ open, the upper surface of petals is Red Group 53D, and the lower surface is Red Group 53C.

*Sepals*.—Size: Average 35 mm long×13 mm wide. Shape: Sepals generally subulate. Sepal apex is generally cirrose. Weak foliaceous appendages on three of the five sepals. Base is flat at union with receptacle. Quantity: Five. Margins: With fine hairs. Surface texture: Covered in fine hairs. Outer surface: Smooth. Stipitate glands are absent. Color: Upper surface Yellow-Green Group 146C. Lower surface Yellow-Green Group 146B.

Receptacle:

*Surface*.—Smooth. With fine hairs.

*Color*.—Yellow-Green Group 146D.

*Shape*.—Campanulate.

*Size*.—15 mm (h)×15 mm (w).

Peduncle:

*Surface*.—Smooth. With stipitate glands.

*Length*.—40 mm average length.

*Diameter*.—4 mm average diameter.

*Color*.—Yellow-Green Group 146D, with intonations of Greyed-Purple Group 185A.

*Strength*.—Strong.

*Borne*.—Singly. 1-2 buds per flowering stem.

Flower bloom:

*Fragrance*.—Light.

*Duration*.—On the plant 10 days. Long lasting. As a cut flower, 7 to 8 days. Senesced petals clinging.

*Size*.—Large flowered garden rose. When open, the average flower diameter is 110 mm and the average flower height is 50 mm.

*Form*.—Shape of flower when viewed from the side: Upon opening, upper part: Convex. Upon opening, lower part: Concave. Open flower, upper part: Flattened convex. Open flower, lower part: Concave.

Color:

*Upon opening, petals*.—Outermost petals: Outer Side: Red Group 53D. Inner Side: Red Group 53D. Innermost petals: Outer Side: Red-Purple Group N57C. Inner Side: Red-Purple Group N57B.

*Upon opening, basal petal spots*.—Basal petal spot, outermost petals: Outer Side: Yellow Group 1B. Inner Side: Yellow Group 1A. Basal petal spot, innermost petals: Outer Side: Yellow-Orange Group 16B. Inner Side: Yellow-Orange Group 16B.

*After opening, petals*.—Outermost petals: Outer Side: Red-Purple Group 67D. Inner Side: Red-Purple Group 65C. Innermost petals: Outer Side: Red-Purple Group 62B. Inner Side: Red-Purple Group 62C.

*After opening, basal petal spots*.—Basal petal spot, outermost petals: Outer Side: Yellow Group 3C. Inner Side: Yellow Group 3C. Basal petal spot, innermost petals: Outer Side: Yellow Group 1B. Inner Side: Yellow Group 1C. Variegations: None.

General tonality: On open flower, Red-Purple Group 58C. No change in the general tonality at the end of the 4$^{th}$ day. Afterwards, general tonality is Red-Purple Group 58D.

Petals:

*Petal count*.—Approximately 150 under normal conditions.

*Petal reflex*.—Petals reflex slightly.

*Petal edge*.—Entire.

*Petal shape*.—Obovate. Apex shape is round. Shape of base is acute.

*Petal size*.—40 mm long; 35 mm wide.

*Thickness*.—Average.

*Petal arrangement*.—Generally in a regular pattern with overlapping edges.

Petaloids: Present.

*Petaloid count*.—Average of 10-12 per flower.

*Petaloid edge*.—Crenate.

*Petaloid texture*.—Smooth.

*Petaloid shape*.—Linear to elliptic.

*Petaloid size*.—Petaloids are 20 mm long and 12 mm wide.

*Petaloid color*.—Color of inner side is Red-Purple Group N57D. Color of outer side is Red-Purple Group N57D.

Reproductive organs:

*Pistils*.—Approximately 50 present. Stigmas: Location: Slightly superior in position to anthers. Color: Gray-Yellow Group 160D. Styles: Length: 10 mm long. Color: White Group 155A. Intonations of Yellow Group 1D.

*Stamens*.—Approximately 55-65 on average and regularly arranged. Anthers: Size: 2 mm long. Color: Yellow Group 4B. Pollen: Generally absent. Filaments: Color: Yellow Group 5B. Length: 8 mm.

THE PLANT

*Plant growth*.—Vigorous. Upright to bushy habit. When grown as a budded nursery plant the average plant height is 130 cm and the average plant width is 80 cm.

*Stems*.—Stem color: Young wood: Yellow-Green Group 146C. Older wood: Yellow-Green Group 146B. Stem surface: Young wood: Smooth. Older wood: Smooth.

*Prickles*.—Present. Incidence: 20-24 per 10 cm of juvenile stem. 7-12 per 10 cm of mature stem. Size: Average length: 8 mm. Color: Immature prickles: Gray-Red Group 181B. Mature prickles: Gray-Brown Group 199B. Senescing to Gray-Orange Group 165A. Shape: Concave. Anthocyanin: Color Gray-Red Group 181A.

*Leaves and leaflets*.—Normally 5-7 leaflets on normal leaves in middle of the stem. Venation pattern: Pyramidal net pattern. Leaf size: 140 mm (l)×90 mm (w). Quantity: Abundant. Texture: Upper side of leaflet: Semi glossy. Smooth. Leathery. Under side of leaflet: Matte. Smooth. Leathery. Color, mature foliage: Upper Leaf Surface: Yellow-Green Group 146A. Lower Leaf Surface: Yellow-Green Group 147C. Color, juvenile foliage: Upper Leaf Surface: Green Group 137B. Lower Leaf Surface: Yellow-Green Group 147C. Anthocyanin intonation: Present. Location: Intonations present on juvenile leaf margins and developing leaves. Color: Gray-Purple Group 183B.

*Stipules*.—Size: 15 mm long. 10 mm between the tips of the stipule. Main body of stipule 4 mm in width. Shape: Longitudinally flanged. Stipule color: Yellow-Green Group 146B. Anthocyanin: Gray-Red Group 181A. Presence of stipitate glands: Present on margins. Margins: With stipitate glands.

*Petiole*.—Length: 25 mm. Diameter: 2 mm. Petiole color: Yellow-Green Group 146B. Anthocyanin present on juvenile tissue. Color: Gray-Red Group 181B. Underneath: Smooth. Stipitate glands: Limited numbers of stipitate glands on margins.

*Petiole rachis*.—Length: 80 mm. Diameter: 2 mm. Color: Yellow-Green Group 146B. Margins: Entire. Prickles: A few small prickles underneath. Stipitate glands: Limited numbers of stipitate glands on margins.

*Leaflets*.—Size: Average size of the terminal leaflet is 55 mm (l)×45 mm (w). Shape: Broadly ovate. Base: Broadly ovate. Apex: Acute. Margins: Finely serrated. Texture: Leathery.

Hips/seed formation: None observed.

Winter hardiness: To date, the variety has been grown successfully in Zone 5.

Disease resistance: Average resistance to Powdery mildew (*Sphaerotheca pannosa* and blackspot (*Diplocarpon rosae*) diseases under normal growing conditions.

I claim:

1. A new and distinct variety of rose plant, as described and illustrated herein.

* * * * *

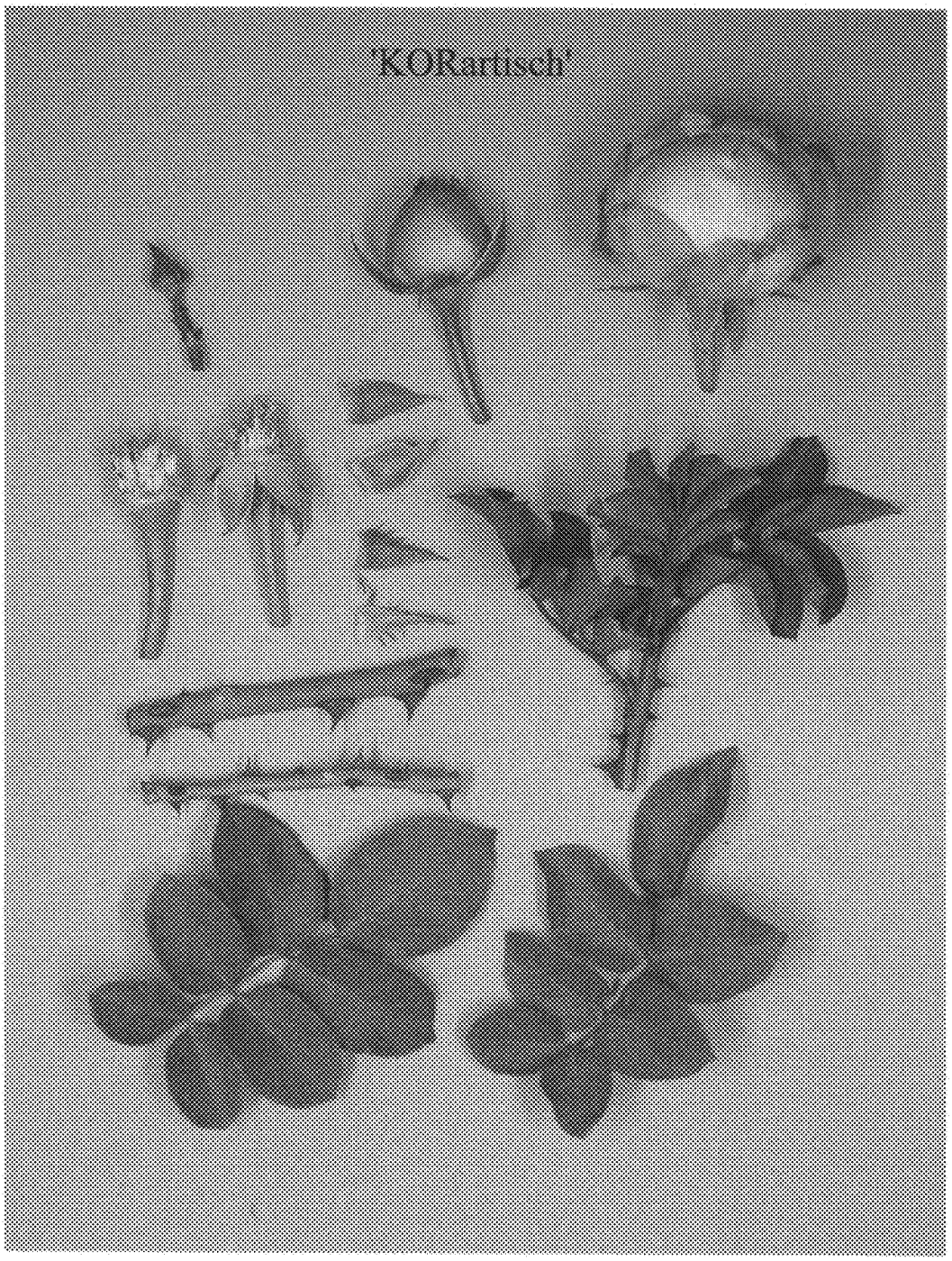
'KORartisch'